United States Patent [19]

Tetenbaum et al.

[11] 4,284,506

[45] Aug. 18, 1981

[54] BIOMEDICAL DEVICES

[75] Inventors: Marvin T. Tetenbaum, Lawrenceville; Barton C. Case, Hightstown, both of N.J.

[73] Assignee: NL Industries, Inc., New York, N.Y.

[21] Appl. No.: 106,571

[22] Filed: Dec. 26, 1979

[51] Int. Cl.³ .................... B01D 31/00; B29C 27/14
[52] U.S. Cl. ................ 210/321.4; 210/493.1;
210/497.1; 422/48; 264/257; 264/261; 264/277;
156/291; 156/292; 156/296; 156/331.3; 260/18
TN; 528/66; 528/80; 156/331.4
[58] Field of Search ............. 210/22 A, 22 C, 22 D,
210/23 R, 23 H, 23 F; 321 R, 321 A, 321 B, 433
M, 493 M, 494 M; 496, 497.1, 500 M, 488;
264/257, 261, 277; 55/16, 158; 422/48; 156/74,
291, 180, 296, 292, 331; 260/18 TN; 528/66, 80

[56] References Cited
U.S. PATENT DOCUMENTS

| | | | |
|---|---|---|---|
| 2,977,385 | 3/1961 | Fowler et al. | 528/80 |
| 3,660,375 | 5/1972 | Kolycheck et al. | 528/80 X |
| 3,962,094 | 6/1976 | Davis et al. | 210/321 R |
| 4,165,287 | 8/1979 | Goyne | 210/321 B X |
| 4,170,559 | 10/1979 | Kropunski et al. | 210/321 A |

*Primary Examiner*—Charles N. Hart
*Assistant Examiner*—David R. Sadowski
*Attorney, Agent, or Firm*—Gary M. Nath; Eugene Striffler

[57] ABSTRACT

The present invention is directed to improved separatory devices employing polyurethane forming compositions, such as hollow fiber separatory devices intended to be used in biomedical applications. The separatory device employs at least one separatory membrane, suitable for the intended end use application, which is secured, potted or sealed in a housing using a cured polyurethane composition. The improvement comprises utilizing as the potting agent a polyurethane composition comprising the reaction product of an NCO-terminated prepolymer and a hydroxy terminated lactone derived polyester. The lactone polyester comprises the reaction product of a lactone such as caprolactone, and a polyol such as 1,6-hexane diol. The lactone derived polyester imparts to the polyurethane-forming composition a desirable balance of properties, including low mix viscosity, high reactivity, i.e., low gel and demold times, and acceptable hardness values, when used as a potting agent in biomedical separatory devices.

10 Claims, No Drawings

BIOMEDICAL DEVICES

BACKGROUND OF THE INVENTION

Separatory devices useful in biomedical applications such as kidney dialysis, hemodialysis, hemoultrafiltration, blood oxygenation and the like are well known. Such devices generally consist of at least one separatory membrane or element, disposed in a housing or casing having an inlet and an outlet means. The separatory membrane may take the form of a hollow fiber, film, screen, and the like and is chosen for its ability to perform the intended biomedical function.

While various methods of manufacture of such separatory devices have been described, certain of such methods employ potting or sealing resins to secure the separatory membranes in the housing and prevent the mixing of fluids which pass on either side of the membrane when necessary.

The suitability of the potting resin for use in a separatory device is governed by a number of criteria which can best be illustrated with reference to separatory devices which employ hollow fibers.

Such devices typically consist of a plurality of permeable hollow fibers whose terminal portions are potted in a sealing collar and extend therethrough, thereby providing liquid access to the interior of the fibers.

The separatory elements are then typically sealed within a casing to form a separatory cell having one or more liquid ports which allow for the passage of one fluid, such as blood, through the fibers and another fluid around the fibers without mixing the two fluids. The separatory element may have two sealing collars or a single sealing collar in which latter case the fibers are doubled back so that all the ends terminate together. The general configuration of the separatory element and separatory cell is similar to a tube-and-shell heat exchanger.

Patents representative of the art of hollow fiber separatory devices include U.S. Pat. Nos. 2,972,349; 3,228,876; 3,228,877; 3,339,341; 3,442,088; 3,423,491; 3,503,515; 3,551,331 the disclosures of which are herein incorporated by reference.

The sealing collar is typically derived from a resin which is capable of encapsulating the fibers to provide a seal which prevents the fluid inside the hollow fibers from mixing with the fluid outside the fibers.

A preferred class of resins useful for preparing the sealing collars are flexible polyurethane forming systems as illustrated by U.S. Pat. Nos. 3,362,921; 3,708,071; 3,722,695; 3,962,094 and 4,031,012 the disclosures of which are herein incorporated by reference. Centrifugal casting, as illustrated by U.S. Pat. No. 3,492,698, the disclosure of which is herein incorporated by reference, is a representative method employed for preparing sealing collars. In accordance with such a technique, a holding device containing a bundle of fibers arranged in a parallel configuration is placed into a centrifugal-like device which incorporates a potting-material reservoir with tubes connecting it to end-molds. An appropriate resin is placed into the potting reservoir maintained at an appropriate temperature. The entire assembly is then rotated to force the resin down the connecting tubes by the centrifugal force. The resin thereby flows around and among the fibers in the end-molds. The rotation is continued until the resin gels. When polyurethanes are employed as the resin, typical residence time in the centrifuge can vary from about 1 to about 2 hours at room temperature. When rotation is completed the resin impregnated fiber bundle is removed and post-cured. The end molds are then removed and the fiber ends are opened by cutting through the resin collar perpendicular to the fiber bundle.

Other sealing collar forming techniques rely on the force of gravity to force the resin into a mold containing the ends of the hollow fibers. The resin is allowed to gel and then is post-cured.

Regardless of the particular method employed for preparing the sealing collar the polyurethanes typically employed therein exhibit extended gel, and demold times.

The same polyurethane resins that are employed in preparing hollow fiber separatory devices are used to perform similar functions in other separatory devices wherein a separatory membrane is provided in a configuration different from that of hollow fibers. Thus, while the configuration of the separatory membranes differ in commercially available separatory devices, the problems of extended cure times are common to all.

In many instances known catalysts that are specific for increasing the hydroxyl-isocyanate reaction rate such as aliphatic and cycloaliphatic tertiary amines, and soluble metal compounds, particularly organotin compounds are employed to increase the generally slow curing time of the polyurethane.

The selection of a suitable catalyst for use in a polyurethane system intended as a potting resin for a biomedical device is complicated by the requirement that the resin system be non-toxic. Thus, the aliphatic and cycloaliphatic tertiary amines are unsuitable because of their toxicity and their use would present a danger that they might be released into the fluids which pass through the separatory device during its operation. Although tin-octoate has been used as a catalyst and is non-toxic it is hydrolytically unstable and must be added to the polyol on site rather than during packaging of the polyol. Ferric acetyl acetonate can also be used as a catalyst but it is toxic at levels of about 0.1% by weight and higher and imparts a dark red color to the polyurethane.

Thus, it would be a distinct advantage if the polyurethane forming composition inherently exhibited a reduced cure time, i.e., gel time and post cure time, even in the absence of a catalyst. This would eliminate the danger posed by incorporation of large amounts of catalysts which can be released into the separatory device.

The choice of a suitable potting resin in the preparation of a separatory device intended for use in a biomedical application is further complicated by the fact that such a resin should optimally also exhibit a number of other important properties such as an acceptably low viscosity, the proper balance between density, flexibility and bonding properties so that the intended sealing effect is achieved e.g., the interior portions of the hollow fibers embedded therein are capable of being hermetically sealed off from the external environment. As described above, the polyurethane must also be non-toxic. This is achieved when the components are completely cured so that residual reactants cannot be released into the fluids which will pass through the separatory device.

The polyurethane should also exhibit avoidance of gas evolution during solidification, a minimum or no change in volume during cure, and a minimum evolution of heat during cure.

The requirement that a potting resin exhibit low viscosity, like the requirement that it exhibit a reduced cure time is a major economic concern. A low mix viscosity of the polyurethane forming system would enable the resin to penetrate efficiently and quickly around and among the hollow fibers when using, for example, the centrifugal casting technique described above. The combination of properties possessed by a polyurethane forming system of low cure time and low viscosity, therefore, would substantially improve the economic efficiency of processes employing the same used in preparing separatory devices.

It is known that polyurethanes may be formed from the reaction of an isocyanate-terminated prepolymer with a lactone derived polyester polyol. Lactone derived polyester polyols may be prepared by reacting a lactone with a polyfunctional alcohol. Such lactone polyesters are well-known and are disclosed in U.S. Pat. Nos. 2,977,385; 3,523,101; 3,591,561; 3,660,357; and 3,663,515, the disclosures of which are herein incorporated by reference as well as British patent specification No. 1,076,871; Belgian Pat. No. 817,879; Japanese Pat. No. 76-76,388; and German Auslegeschrift No. 1,936,587. For example, U.S. Pat. No. 2,977,385 discloses lactone adducts which are useful in preparing polyurethanes, as plasticizers, and as intermediates for preparing elastomers and foams. The lactone adducts are prepared by reacting a lactone having at least six carbon atoms in the ring with any of a number of initiators. These initiators include monofunctional alcohols, monofunctional amines, diols and higher functional alcohols, polyamines, etc. The use, however, of polyurethanes prepared from such lactone adducts as potting compositions in separatory devices is not disclosed in any of the above patents.

The search has therefore continued for ways to improve the cost efficiency of separatory devices intended for use in biomedical applications and processes for preparing the same. The present invention is a result of this search.

SUMMARY OF THE INVENTION

In one aspect of the present invention there is provided an improved separatory device capable of use in a biomedical application wherein at least one separatory membrane is secured in a housing, in a manner sufficient to perform the selected biomedical function, by means of a cured polyurethane composition provided by reacting a first component comprising an NCO-terminated prepolymer with a second component comprising at least one polyol.

The improvement comprises using as the polyurethane composition the reaction product of at least one of said NCO-terminated prepolymers and at least one hydroxyl-terminated lactone polyester comprising the reaction product of at least one lactone represented by the structural formula:

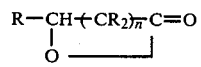

wherein n is an integer which can vary from 1 to about 10, and R is selected from the group consisting of hydrogen, alkyl, cycloalkyl, and alkoxy groups, having from about 1 to about 6 carbon atoms, and at least one saturated difunctional polyol selected from the group consisting of (a) glycols represented by the structural formula:

wherein n is an integer which can vary from about 0 to about 12, and R' is selected from the group consisting of hydrogen and an alkyl group having from about 1 to about 6 carbon atoms; and (b) cycloaliphatic polyols represented by the structural formula:

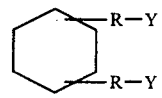

wherein R is an alkyl group having from about 1 to about 6 carbon atoms and Y is a primary hydroxyl group.

In another aspect of the present invention there is provided an improvement in the process for preparing the above separatory device. The improvement comprises reacting the above described lactone polyester with an NCO-terminated prepolymer.

DESCRIPTION OF THE PREFERRED EMBODIMENTS

The separatory devices of the present invention and the process for preparing the same embody a two component polyurethane forming composition which comprises as the first component at least one NCO-terminated prepolymer and as the second component at least one lactone derived polyester polyol.

The NCO-terminated prepolymer is formed from the reaction product of at least one polyfunctional alcohol and at least one polyfunctional isocyanate. The proper selection of the reactants which are employed to prepare the NCO-terminated prepolymer for non-toxic use in a biomedical device is well within the skill in the art when guided by the above requirements described herein for the potting resin.

Thus, representative examples of the polyisocyanates which may be employed in the preparation of the NCO-terminated prepolymer include aromatic isocyanates as illustrated by the di- and tri-isocyanates of the benzene and naphthalene series and mixtures thereof. Illustrative of aromatic isocyanates that may be employed include diphenylmethane 4,4'-diisocyanate (MDI); toluene diisocyanate (2,4/2,6); toluene 2,4-diisocyanate; toluene 2,6-diisocyanate; m-phenylene diisocyanate; xenylene 4,4'-diisocyanate; naphthalene 1,5-diisocyanate; diphenylene 4,4'-diisocyanate; diphenylene ether 4,4'-diisocyanate; and 4,4',4''-triphenylmethane triisocyanate. Polymeric isocyanates such as polymethylene polyphenylene polyisocyanates can be employed when the absence of color is not a requirement. Other aromatic diisocyanates which are useful include lower alkyl substituted derivatives, and alkoxy derivatives.

Aliphatic diisocyantes such as 3-isocyanatomethyl-3,5,5-trimethylcyclohexylisocyanate (IPDI), 4,4'-dicyclohexylmethane diisocyanate, hexamethylene-1,6-diisocyanate, and trimethyl hexamethylene diisocyanate may also be used. Other aromatic and aliphatic isocyanates as well as mixtures, may also be used in the prepolymer preparation.

Representative polyols used to react with the isocyanates to form the NCO-terminated prepolymer include castor oil; polyether polyols (i.e., hydroxy terminated) including the adducts of propylene oxide or ethylene oxide and at least one polyol, the latter being illustrated by propylene glycol, trimethylol propane, 1,2,6-hexane triol, glycerine and pentaerythritol; and polytetramethylene ether glycols.

Commerical grades of castor oil are generally suitable herein for use in the prepolymer formation. Castor oil is a naturally occurring triglyceride of ricinoleic acid and thus contains at least three hydroxy groups. While the composition of castor oil cannot be precisely defined, it is generally accepted that its ester groups are usually 80–92% ricinoleic, 3–7% linoleic, 0–9% oleic and 0–1% palmitic.

Polyol ester derivatives provided by reacting dihydric lower aliphatic polyols with aliphatic dicarboxylic acids, anhydrides, or hydroxy carboxylic acids are also suitable for preparing the prepolymer. Representative examples of aliphatic dihydric alcohols suitable for preparing polyester polyols include ethylene glycol, propylene glycol, hexylene glycol, diethylene glycol, dipropylene glycol, and hexamethylene glycol. The hydroxy carboxylic acids suitable for preparing polyol monoesters may be saturated or unsaturated. Illustrative of the class of hydroxy acids which may be employed include ricinoleic acid, 12-hydroxy stearic acid, hydroxy palmitic acid, hydroxy pentadecanoic acid, hydroxy myristic acid, hydroxy docosanoic acid, hydroxy cerotic acid, etc. Illustrative of aliphatic carboxylic acids include adipic, glutaric, pimelic, malonic, fumaric acids and the like.

The preferred polyol ester derivatives are provided from ricinoleic acid such as ethylene glycol monoricinoleate.

The isocyanate and polyol typically are reacted at NCO/OH equivalent weight ratio of from about 2:1 to about 12:1, and preferably from about 4:1 to about 7:1.

The preferred NCO-terminated prepolymer comprises the reaction product of a mixture of polyoxypropylene glycol and castor oil with (1) diphenylmethane 4,4-diisocyanate (MDI) or (2) a mixture of MDI with 3-isocyanatomethyl-3,5,5-trimethylcyclohexylisocyanate.

The lactone derived polyester polyols which are employed as the second polyol component and which possess and impart the unexpected properties described herein to the polyurethane composition are the reaction products of a lactone and a polyfunctional alcohol.

The lactone used in preparing the polyester polyol may be any lactone or combination of lactones having at least 3 carbon atoms in the lactone ring and can be represented by the structural formula:

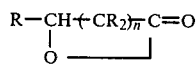

wherein n is an integer of at least 1 and typically can vary from about 1 to about 10, preferably from about 3 to about 10, and most preferably from about 5 to about 10, R is selected from the group consisting of hydrogen, alkyl, cycloalkyl, and alkoxy, radicals having from about 1 to about 6, preferably from about 1 to about 3 carbon atoms. Preferably, at least (n+2)R groups are hydrogen. Representative examples of such substituents include methyl, ethyl, propyl, isopropyl, methoxy, ethoxy, and cyclohexyl radicals.

The preferred lactone is caprolactone.

The polyfunctional alcohol employed in preparing the lactone derived polyester polyol are limited to saturated aliphatic and cycloaliphatic primary alcohols which have an hydroxyl functionality of at least 2. Such alcohols include glycols of the formula:

wherein n is an integer which can vary from 0 to about 12; preferably from about 0 to about 8, and most preferably from about 0 to about 4, and R' can be hydrogen, or alkyl having from about 1 to about 6, preferably from about 1 to about 3 carbon atoms.

Representative examples of such glycols include ethylene glycol; 1,4-butane diol; 1,6-hexane diol; 1,5-pentane diol; 1,7-heptane diol; 1,8-octane diol; 1,9-nonane diol; neopentyl glycol and the like.

The primary saturated cycloaliphatic alcohols can be represented by the structural formula:

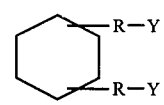

wherein R is an alkyl group having from about 1 to about 6 carbon atoms, preferably from about 1 to about 3 carbon atoms and Y is a primary hydroxyl group.

Illustrative examples of suitable alcohols represented by structural formula III include 1,4-cyclohexane dimethanol and 1,4-cyclohexane diethanol.

Other suitable primary alcohols include those having a functionality of greater than two such as trimethylolethane, trimethylolpropane, triethanolpropane and pentaerythritol.

The preferred polyfunctional alcohols used in preparing the lactone derived polyester include 1,6-hexane diol; 1,5-pentane diol; 1,4-cyclohexane dimethanol, trimethylolethane, and neopentyl glycol.

The preferred lactone derived polyester polyol is the reaction product of caprolactone and 1,6-hexane diol.

The lactone and polyfunctional alcohol are reacted at a molar ratio of from about 1:1 to about 1:3, and preferably from about 1:1 to about 1:2.

Processes for preparing lactone polyester polyols are well known, as disclosed in U.S. Pat. Nos. 2,933,477; 2,933,478; 3,591,561; and 2,914,566, which have previously been incorporated by reference. The lactone polyesters of the present invention can be conveniently prepared by mixing together at least one lactone, preferably caprolactone, and at least one polyfunctional alcohol, and heating the mixture to a temperature of from about 160° C. to about 225° C., and preferably about 180° C. to 205° C. The reactants are charged to the reaction vessel under a nitrogen atmosphere, along with a small amount of toluene, which forms an azeotrope with whatever water is present, thereby providing a "dry" reaction system. After cooling the resulting solution to approximately 180° C., a catalytic amount of benzoyl chloride is added. The solution is maintained at approximately 180° to 185° C. for approximately 7 to 10 hours until reaction is complete as indicated by disappearance of lactone, which can be measured, for example, by gas chromatography.

The reaction of lactone and polyol can also be catalyzed by p-toluenesulfonic acid. Stoichiometric amounts of lactone and alcohol are reacted in the presence of approximately 0.5% by weight of p-toluenesulfonic acid by heating and stirring at approximately 125° to 160° C. for approximately 4 to 6 hours. The cooled product is diluted with an equal volume of chloroform and extracted with 10% sodium bicarbonate solution to remove catalyst. The solvent is then stripped, e.g., on a rotary evaporator, to afford a good yield of light yellow polyols.

In the reaction of lactone with polyfunctional alcohol, the polyol is believed to open the lactone ring to produce an adduct having terminal hydroxy groups which are capable of opening further lactone rings, thereby adding more and more lactone to the molecule.

The molecular weight of the polymers resulting from reaction of the polyol and caprolactone may be conveniently determined from the average number of carboxyl and hydroxyl groups in a given amount of the polyester. The acid number (milligrams of KOH per gram of polyester using phenolphthalein as an indicator) is a measure of the number of terminal carboxyl groups in a polyester. The hydroxyl number, which is a measure of the number of terminal hydroxyl groups and is defined in terms of milligrams of KOH per gram of polyester, is determined by adding pyridine and acetic anhydride to the polyester and titrating the acetic acid formed with KOH as described in Ind. Eng. Chem., Anal. Ed., vol. 16, page 541-9, and in Ind. Eng. Chem., Anal. Ed., Vol. 17, page 394. The sum of the acid or carboxyl number and the hydroxyl number, referred to as the reactive number, is an indication of the average number of terminal groups present in the polyester and therefore is in turn an indication of the number of molecules in the mass and the degree of polymerization. A polyester containing long chain molecules will have a relatively low reactive number while a polyester containing short chain molecules will possess a relatively high reactive number.

It is preferred to select the starting lactones and polyol and their relative proportions so as to produce polyesters having a carboxyl number as low as possible, e.g., less than about 2, and preferably less than about 1, and a hydroxyl number between about 100 and about 600, preferably between about 225 and about 500 so that the number average molecular weight of the polyester will be in the range of about 200 to about 1,000 and preferably from about 200 to about 500.

The appropriate molecular weight is selected to impart the optimum properties to the polyurethane composition.

The amount of lactone derived polyester polyol added to the NCO-terminated prepolymer composition should be sufficient to react with the free isocyanate groups remaining after the preparation of the prepolymer, but preferably not too low or too large an excess is used. Too low an amount may result in a cured system which is too hard while excess amounts may result in undesired plasticizer action. The proper amount of crosslinking agent required to react properly with the prepolymer can readily be determined by those skilled in the art by known calculations.

Accordingly, the NCO-terminated prepolymer is preferably blended with the lactone derived polyester polyol at weight ratios of from about 20:80 to about 80:20 and preferably from about 30:70 to about 65:35 respectively.

The polyurethanes suitable for use in the devices of the present invention are preferably not prepared by reacting a lactone, a polyol, and an NCO-terminated prepolymer in a single step. In such a reaction, some of the hydroxyl groups of the polyol react directly with isocyanate groups, yielding a polyurethane lacking the advantageous properties of the polyurethanes employed in the present invention.

Polyurethane compositions prepared as described above and comprising the reaction product of at least one NCO-terminated prepolymer and at least one of the lactone derived polyester polyols of the present invention are characterized by a balance of properties making them unexpectedly advantageous for use as potting agents in biomedical devices prepared by the centrifugal casting method.

When the lactone derived polyester polyol is mixed with the NCO-terminated prepolymer the resulting composition is characterized by a low mix viscosity which promotes easy penetration thereof where desired, e.g., among and around the hollow fibers.

The mix viscosity of the polyurethane is the viscosity, as determined by a standard Brookfield viscosity measurement, of the mixture of the NCO-terminated prepolymer and lactone polyester, measured two minutes after mixing. The polyurethane compositions of the present invention have a mix viscosity of less than about 4000 cps, preferably less than about 2500 cps and most preferably less than about 1000 cps.

The reactivity of the polyurethane forming composition is also characterized by improved gel time, non-flow time, and demold time.

To determine the gel time, a sample (e.g., 50 gms) of the prepolymer/lactone derived polyester polyol mixture is placed in a 50 ml. beaker. A round wooden splint is used to break the surface of the mixture and is then withdrawn. The process of breaking the surface and withdrawing the splint is repeated continuously. The gel time is the point in time at which a string of polymer is no longer pulled from the mixture as the splint is withdrawn. The polyurethane forming compositions of the present invention have gel times of not greater than about 60 minutes and typically from about 10 to about 60 minutes, and preferably from about 10 to about 20 minutes.

To measure the non-flow time, the beaker is placed on its side as the mixture polymerizes. The non-flow time is the point in time at which the polymer does not sag or drip after the beaker has been on its side for 30 seconds. The polyurethane compositions of the present invention have non-flow times at 25° C. of about 10 to about 60 minutes, and preferably of about 10 to about 30 minutes.

The plug of polymer is removed from the beaker to measure the demold time. Soon after removal from the beaker, the polymer has a fluid feel and will be penetrated when pressed with the finger. The demold time is the time, after mixing, in which the polymer plug begins to feel resilient, rather than fluid and resists finger penetration. The polyurethane compositions of the present invention have demold times at 25° C. of from about 15 to about 240 minutes and preferably from about 15 to about 30 minutes.

The low viscosity and high reactivity of the polyurethane forming compositions which are suitable for use in the separatory devices of the present invention allow a substantial reduction in the time required to fabricate the devices by the centrifugal casting technique. Moreover, because of the high reactivity of the lactone polyesters with the NCO-terminated prepolymer, the polymerization does not require the use of a catalyst to render the separatory device and process for preparing the same cost efficient. The catalysts ordinarily employed in the reaction of an NCO-terminated prepolymer with a polyol, as described above, when present in a large amount, present potential toxicity problems when the resulting polyurethane is used in separatory devices having biomedical applications. The absence of a catalyst in the present system eliminates such potential problems.

It is a further advantage of the polyurethane forming compositions described herein that the polyurethane forming composition is much more responsive to the presence of a catalyst than other systems of the prior art because of their high reactivity. Therefore, if a catalyst must be used at all, the amounts employed (e.g., less than about 2%, preferably from about 0.2% to about 1%) to produce a substantial catalytic effect are much smaller than the amounts required by conventional polyurethane systems, thereby substantially reducing potential toxicity problems.

Suitable catalysts include dibutyltin dilaurate and a tertiary amine accelerator derived from ricinoleic acid and having the following structure:

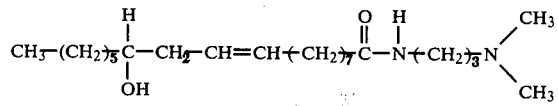

The cured polyurethane compositions have acceptable hardness values for use in biomedical separatory devices. The hardness of the completely-reacted polymer is measured by the standard ASTM D2240-75 test. The cured compositions exhibit a shore hardness of from 40A to 85D, and preferably of from about 50D to about 70D.

In addition to the above-described properties, the polyurethane compositions employed in the devices of the present invention demonstrate a light color, good hydrolytic stability, low temperature resistance and are not brittle.

In preparing hollow fiber separatory devices which are adaptable to the catalyzed polyurethane forming composition, the hollow fibers can be provided from any of a wide variety of polymers well known in the art to be suitable for biomedical applications. Such fibers include those which are prepared from compounds which contain —OH, —NH$_2$, and =NH groups.

Representative examples of such compounds include cellulose, cellulose acetate, cellulose ethers, polyamides, polyacrylamides, polysulfones, polyesters, polycarbonates, polyurethanes, polysacchrides, and proteins in general, such as casein, collagen and the like. Preferred fibers include cellulose and cellulose acetate.

As described above, the sealing collar for hollow fiber separatory devices may be formed in a number of ways well known in the art, with the preferred method being centrifugal casting, as illustrated in U.S. Pat. No. 3,492,698.

Generally, hollow fibers are fabricated into a substantially parallel bundle of from about 1,000 to 20,000 or more fibers by a number of methods. One such method is to wrap a fiber continuously end-to-end onto a mandrel rod with retaining brackets on either end. The substantially parallel fibers are then inserted into a holding device with end-molds as described in the aforementioned U.S. Pat. No. 3,492,698.

The polyurethane forming compositions will typically be cured in two stages. In the first stage, referred to herein as the pre-cure, they are subjected to temperatures of from about 25° to about 75° C., and preferably from about 25° to about 50° C. The polyurethane composition is considered to be pre-cured when it has gelled to the point that it will not flow as determined by the gel test discussed herein. The manner in which the resin is pre-cured can vary and will depend on the particular apparatus employed to make the hollow fiber separatory device.

For example, the holding device containing the fiber bundle is typically placed into a centrifuge-like device which incorporates a potting-material reservoir with tubes connecting it to the end-molds. The mixture of the lactone polyester polyol component, and the NCO-terminated prepolymer can be mixed and placed into the potting reservoir wherein it is maintained at the above described pre-cure temperatures, and the entire assembly then rotated to provide a 2 to 200 g force nearly parallel to the fiber bundle. The resin is forced down the connecting tubes by the g force and flows around and among the fibers in the end-molds. The end-molds can optionally also be heated to the above-described pre-cure temperatures. The process is continued until the reservoir is devoid of resin. Alternatively, the potting material can be placed into the holding device at room temperature and forced into the end-molds which are heated to the above described pre-cure temperatures.

The rotation is continued until the polyurethane is gelled, i.e., has set to a non-flowable state.

The use of the lactone polyesters permits a reduction in centrifuge times (i.e., gel or pre-cure times) to from about 5 to about 30 minutes, preferably from about 10 to about 25 minutes (e.g., 20 minutes) at the above described pre-curing temperatures. Higher pre-curing temperatures up to about 75° C. permit increasingly shorter centrifuge times. Room temperature pre-cures are preferred since this results in a substantial savings in energy consumption and cost by reducing the time during which the centrifuge is tied up for each batch of hollow fibers relative to that required when using conventional polyols.

After the polyurethane has pre-cured (i.e. gelled) the fiber bundle is removed and the unit placed in an oven for the second stage of curing referred to herein as post-curing. Post-curing temperatures can vary from about 25° C. to about 75° C., and preferably from about 45° to about 65° C. (e.g., 50° C.). Post-curing times also referred to herein as demold times, can vary from about 30 to about 180 minutes, and preferably from about 30 to about 60 minutes at the above described post-curing temperatures.

Alternatively, pre-curing and post-curing can be achieved in a single stage by permitting the resin to remain at temperatures of about 25° to about 75° C. for a period of about 10 to about 180 minutes (e.g. 60 minutes).

The end-molds are then displaced and the potted fibers are opened by cutting through the sealing collar perpendicular to the fiber bundle. A bundle results wherein the potted end or ends demonstrate structural integrity and round, open fibers.

While the present disclosure is directed primarily to hollow fiber separatory devices which employ the polyurethane forming composition described herein, the present invention also contemplates the use of the aforementioned composition in conjunction with the above described curing temperatures and times in any separatory device to be used in biomedical applications which requires the sealing of a separatory membrane in a nontoxic potting resin. The term separatory membrane as employed herein characterizes the configurations into which a substance can be provided to perform the function of selecting, filtering, or separating, one material from a medium containing the same and includes such configurations, in addition to hollow fibers, as films, screens, foams, sponges, and the like.

Such separatory devices include those which can be employed as blood transfusion filters such as depth filters, screen filters, and combination depth and screen filters. In the depth type filter, blood passing through the interstices of the filter is exposed to a large foreign surface, and microaggregates in the blood (e.g., platelets, white cells, and matted fibrin) are removed by adhesion to the filtering medium. Screen type filters effect filtration by sieving, i.e., by mechanically obstructing passage of particles larger than the screen pore size. The combination type filters combine the filtration modes of both depth and screen filters. Representative separatory membranes which can be employed in such blood transfusion devices include those prepared from Dacron wool, polyester mesh, polyurethane sponge and foam, nylon wool and the like. Each of these separatory membranes can be secured in a filter housing using the polyurethane forming compositions described herein.

Another broad group of separatory devices employing separatory membranes which can be potted or sealed with the polyurethanes described herein are those which employ permeable or selectively permeable films. The identity of the composition of such films is selected in accordance with well known requirements for their ability to perform an intended function such as blood oxygenation, kidney dialysis, and the like. Such devices typically comprise a plurality of membranes (e.g., films) disposed in a spaced relationship in opposition to one another, e.g., in a substantially parallel, pleated, concentric or spiral surface-to-surface array, so as to define both a first group of flow volumes (e.g., to permit the flow of blood) and a second group of volumes (e.g., to permit the flow of a treating fluid). The members of the second group of flow volumes are disposed in alternating relationship with the members of the first group. Each flow volume contains membrane-spacing means (e.g., a woven screen) to support the membranes which define the two groups of flow volumes.

Means are provided for simultaneously defining the periphery of each of said flow volumes and for bonding together adjacent membrane assemblies, and the spacing means located therebetween to form gas-tight peripheral walls. In the present invention, such means comprise the catalyzed polyurethane described herein. The techniques for employing the potting resin in such devices are well known in the art.

Means are also provided for separate access to and egress from the first and second group of flow volumes. The access and egress means, which typically take the form of discontinuous channels, place at least two adjacent flow volumes of the same group in flow communication. The entire assembly is located in, or defines, a housing with a feed inlet and a feed outlet in flow communication with the access and egress means, respectively, of each group of flow volumes.

Representative patents which illustrate such separatory devices include U.S. Pat. Nos. 3,879,293, 3,907,687 and 3,925,037 the disclosures of which are herein incorporated by reference.

The invention is additionally illustrated in connection with the following Example which is to be considered as illustrative of the present invention. It should be understood, however, that the invention is not limited to the specific details of the Example. All parts and percentages in the claims and in the remainder of the specification are by weight unless otherwise specified.

EXAMPLE 1

The following NCO-terminated prepolymers are prepared in the following manner.

Prepolymer A

A mixture of 204 gms of polyoxypropylene glycol having a number average molecular weight of 400, 205 grams of castor oil, 614 grams of diphenylmethane-4,4'-diisocyanate (MDI) and 181 grams of 3-isocyanatomethyl-3,5,5-trimethylcyclohexylisocyanate (IPDI) are charged to a reactor under a nitrogen blanket and with agitation. The temperature is slowly raised to 75° C. and maintained at 70°–80° C. for 2 hours cooling when necessary. The resulting prepolymer has an NCO content of about 17.4% and a viscosity of about 4000 cps.

Prepolymer B

In accordance with the procedure for preparing prepolymer A above, a second prepolymer is prepared based upon: 204 grams polyoxypropylene glycol having a number average molecular weight of 400, and a sufficient amount of MDI to bring the NCO content of the resulting prepolymer to 20.5% and a viscosity of about 4000 cps.

Preparation Of Lactone Derived Polyester Polyol

A number of different lactone derived polyester polyols are prepared by reacting E-caprolactone with various polyols as shown at Table I, Col. 1. The molar ratios at which the polyol and lactone are reacted are also shown at Table I, Col. 2. In some instances the resulting lactone polyester is mixed with another lactone polyester. The %, by weight, of each polyester in the mixture as shown at Table I, Col. 3 where applicable. The hydroxyl and acid numbers of each resulting lactone polyester are provided at columns 4 and 5.

The general procedure for the preparation of each lactone polyester is as follows.

A four-necked resin kettle is equipped with a stirrer, condenser, Dean-Stark water trap, nitrogen sweep, and thermocouple. Stoichiometric amounts of caprolactone and with the appropriate alcohol are charged, along with a small amount of toluene (100 ml toluene per 2,000 g. reaction mixture), to the reaction vessel.

The identity of each polyol and molar ratio of lactone to polyol for each run are given in Table I. Each mixture is stirred and heated at 195°–200° C. under a nitrogen atmosphere while toluene azeotropes the system dry. The resulting solutions are cooled to 180° C., and catalytic benzoyl chloride is added (0.35 ml. benzoyl chloride per 1,000 g. reaction mixture). Using a slow nitrogen sweep and good stirring, each solution is maintained at 180°–185° C. while monitoring lactone disappearance by gas chromatography. When each reaction is complete (7-10 hours), each lactone polyester is held at 120° C. for 1 hour at 15 mm. pressure and then sparged with nitrogen at 100° C. and 15 mm. pressure for an additional hour. High yields of clear, almost colorless lactone polyesters are obtained with water levels below 0.05%.

Each lactone derived polyester or mixture thereof is then hand mixed for one minute with either prepolymer A or B as shown at Table I, Column 6 in amounts sufficient to achieve an NCO/OH equivalent ratio of about 1.1/1.0 resulting in a 10% NCO equivalent excess.

Samples of each mixture are then tested for mix viscosity 2 minutes after mixing, gel time and demold time in accordance with the procedures defined herein.

As may be seen from the data of Table I the balance of properties of mix viscosity, gel time and demold time are good for all the samples tested.

TABLE 1

| Col No | 1 | 2 | 3 | 4 | 5 | 6 | 7 | 8 | 9 | 10 |
|---|---|---|---|---|---|---|---|---|---|---|
| Run No. | Polyol | Polyol: -Caprolactone Molar Ratio | % of Each Component in Lactone Polyester Polyol Mixture | Hydroxyl No. of Lactone Polyester | Acid No. of Lactone Polyester | NCO-Terminated Prepolymer Type | 2 Min. Mix Viscosity at 25° C. | Gel Time (min: sec) | Non-flow Time (min: sec) | Demold Time (min: sec) |
| 1 | HO—(CH$_2$)$_6$—OH | 1:1 | N/A | 467.7 | 0.27 | A | 1650 | 10:20 | 13:30 | 35:00 |
| 2 | HO—(CH$_2$)$_6$—OH | 1:2 | N/A | 312.5 | 0.48 | A | 920 | 25:00 | 42:00 | 237:00 |
| 3 | HO—(CH$_2$)$_5$—OH | 1:1 | N/A | 491.2 | 0.43 | A | 1250 | 14:15 | 17:00 | 32:00 |
| 4 | HO—(CH$_2$)$_5$—OH | 1:2 | N/A | 343.8 | 0.77 | A | 1100 | 32:10 | 40:00 | 63:00 |
| 5 | CHDM | 1:1 | N/A | 420.1 | 0.56 | A | 3850 | 12:45 | 15:30 | 21:00 |
| 6 | CHDM | 1:2 | N/A | 292.2 | 0.67 | A | 2400 | 27:15 | 34:30 | 53:00 |
| 7 | NEOP | 1:1 | N/A | 490.6 | 0.47 | A | 2050 | 30:00 | 38:00 | 50:00 |
| 8 | NEOP | 1:2 | N/A | 321.7 | 1.20 | A | 1800 | 55:00 | 88:00 | 120:00 |
| 9 | HO—(CH$_2$)$_4$—OH | 1:1 | N/A | 504.6 | 2.30 | A | 1600 | 15:00 | 20:25 | 29:35 |
| 10 | HO—(CH$_2$)$_4$—OH | 1:2 | N/A | 311.5 | 0.37 | A | 1700 | 28:40 | 36:35 | 54:50 |
| 11 | HO—(CH$_2$)$_6$—OH | 1:1 | N/A | 467.7 | 0.27 | B | 727 | 11:00 | 14:00 | 24:00 |
| 12 | CHDM | 1:1 | N/A | 420.1 | 0.55 | B | 2750 | 9:30 | 12:55 | 16:40 |
| 13 | TMP HO—(CH$_2$)$_6$—OH | 1:1 1:1 | 15 85 | 659.0 467.7 | 1.08 0.27 | A | 1510 | 13:06 | 15:30 | 34:00 |
| 14 | TMP HO—(CH$_2$)$_6$—OH | 1:1 1:1 | 30 70 | 659.0 467.7 | 1.08 0.27 | A | 2098 | 13:00 | 15:00 | 33:00 |
| 15 | TMP HO—(CH$_2$)$_6$—OH | 1:1 1:1 | 50 50 | 659.0 467.7 | 1.08 0.27 | A | 3425 | 14:00 | 16:00 | 36:00 |
| 16 | TMP HO—(CH$_2$)$_6$—OH | 1:1 1:1 | 15 85 | 659.0 467.7 | 1.08 0.27 | B | 1030 | 10:45 | 12:30 | 21:00 |
| 17 | TMP HO—(CH$_2$)$_6$—OH | 1:1 1:1 | 30 70 | 659.0 467.7 | 1.08 0.27 | B | 1196 | 10:35 | 12:50 | 21:00 |
| 18 | TMP HO—(CH$_2$)$_6$—OH | 1:1 1:1 | 50 50 | 659.0 467.7 | 1.08 0.27 | B | 1546 | 10:00 | 12:45 | 20:00 |
| 19 | TMP CHDM | 1:1 1:1 | 15 85 | 659.0 420.1 | 1.08 0.56 | B | 2588 | 9:50 | 13:00 | 17:00 |
| 20 | TMP CHDM | 1:1 1:1 | 30 70 | 659.0 420.1 | 1.08 0.56 | B | 2955 | 11:40 | 14:30 | 20:00 |
| 21 | TMP CHDM | 1:1 1:1 | 50 50 | 659.0 420.1 | 1.08 0.56 | B | 3500 | 10:30 | 13:30 | 20:00 |
| 22 | TME HO—(CH$_2$)$_6$—OH | 1:1 1:1 | 15 85 | 617.0 467.7 | 0.81 0.27 | A | 1614 | 13:50 | 18:00 | 44:00 |
| 23 | TME HO—(CH$_2$)$_6$—OH | 1:1 1:1 | 30 70 | 617.0 467.7 | 0.81 0.27 | A | 1790 | 14:10 | 18:30 | 29:30 |
| 24 | TME HO—(CH$_2$)$_6$—OH | 1:1 1:1 | 50 50 | 617.0 467.7 | 0.81 0.27 | A | 2900 | 15:30 | 21:30 | 38:00 |
| 25 | TME HO—(CH$_2$)$_6$—OH | 1:1 1:1 | 15 85 | 617.0 467.7 | 0.81 0.27 | B | 706 | 9:00 | 12:45 | 20:54 |
| 26 | TME HO—(CH$_2$)$_6$—OH | 1:1 1:1 | 30 70 | 617.0 467.7 | 0.81 0.27 | B | 848 | 10:20 | 12:30 | 20:00 |
| 27 | TME HO—(CH$_2$)$_6$—OH | 1:1 1:1 | 50 50 | 617.0 467.7 | 0.81 0.27 | B | 1492 | 11:00 | 13:00 | 19:00 |
| 28 | TME CHDM | 1:1 1:1 | 15 85 | 617.0 420.1 | 0.81 0.56 | B | 2314 | 9:00 | 12:00 | 19:50 |
| 29 | TME CHDM | 1:1 1:1 | 30 70 | 617.0 420.1 | 0.81 0.56 | B | 2534 | 11:10 | 14:00 | 24:00 |
| 30 | TME CHDM | 1:1 1:1 | 50 50 | 617.0 420.1 | 0.81 0.56 | B | 2575 | 11:50 | 16:30 | 24:50 |
| 31 | HO—(CH$_2$)$_6$—OH HO—(CH$_2$)$_6$—OH | 1:2 1:1 | 15 85 | 312.5 467.7 | 0.48 0.27 | A | 940 | 14:00 | 20:10 | 55:00 |
| 32 | HO—(CH$_2$)$_6$—OH HO—(CH$_2$)$_6$—OH | 1:2 1:1 | 30 70 | 312.5 467.7 | 0.48 0.27 | A | 854 | 16:00 | 27:00 | 180:00 |
| 33 | HO—(CH$_2$)$_6$—OH HO—(CH$_2$)$_6$—OH | 1:3 1:1 | 15 85 | 232.3 467.7 | 0.51 0.27 | A | 980 | 14:30 | 18:30 | 52:00 |
| 34 | HO—(CH$_2$)$_6$—OH HO—(CH$_2$)$_6$—OH | 1:2 1:1 | 15 85 | 312.5 467.7 | 0.48 0.27 | B | 525 | 11:30 | 14:20 | 27:30 |
| 35 | HO—(CH$_2$)$_6$—OH HO—(CH$_2$)$_6$—OH | 1:2 1:1 | 30 70 | 312.5 467.7 | 0.48 0.27 | B | 521 | 12:50 | 16:30 | 33:00 |
| 36 | HO—(CH$_2$)$_6$—OH HO—(CH$_2$)$_6$—OH | 1:2 1:1 | 50 50 | 312.5 467.7 | 0.48 0.27 | B | 483 | 15:00 | 21:30 | 57:00 |

TABLE 1-continued

| Col No | 1 | 2 | 3 | 4 | 5 | 6 | 7 | 8 | 9 | 10 |
|---|---|---|---|---|---|---|---|---|---|---|
| Run No. | Polyol | Polyol:-Caprolactone Molar Ratio | % of Each Component in Lactone Polyester Polyol Mixture | Hydroxyl No. of Lactone Polyester | Acid No. of Lactone Polyester | NCO-Terminated Prepolymer Type | 2 Min. Mix Viscosity at 25° C. | Gel Time (min: sec) | Non-flow Time (min: sec) | Demold Time (min: sec) |
| 37 | HO—(CH$_2$)$_6$—OH | 1:2 | N/A | 312.5 | 0.48 | B | 576 | 20:20 | 26:00 | 61:00 |

N/A = Not Applicable
CHDM = 1,4-Cyclohexanedimethanol
NEOP = Neopentyl Glycol
TMP = 1,1,1-Trimethylolpropane
TME = 1,1,1-Trimethylolethane

COMPARATIVE EXAMPLE

Example 1 is repeated with the exception that common polyols typically used in polyurethane forming systems are employed instead of the lactone derived polyester polyols of the present invention. The polyol and the associated NCO-terminated prepolymer are shown at Table II. Prepolymer C is prepared in accordance with the procedures employed in the preparation of prepolymer A of Example 1 based upon 204 gms of polyoxypropylene glycol having a number average molecule weight of 400, 205 gms of castor oil, and 795 gms of diphenylmethane-4,4′-diisocyanate. The resulting prepolymer has an NCO content of about 16.2%, and a viscosity of about 6000 cps.

Runs 3 to 6 employ prepolymer A of Example 1.

As may be seen from the data of Table II the overall balance of measured properties of the comparative polyurethane forming systems are substantially below those of the subject invention.

TABLE II

| Run No. | Polyol | NCO-Terminated Prepolymer | 2 Min. Mix Viscosity at 25° C. | Gel Time (min) | Non-flow Time (min) | Demold Time (min) |
|---|---|---|---|---|---|---|
| 1 | Castor oil modified[1] pentaerythritol | Prepolymer C | 3,500 | 65 | 70 | 360 |
| 2 | Pentaerythritol mono ricininoleate | Conothane 2000[2] | 30,000 | 240 | 960 | 3 days |
| 3 | Polyoxypropylene glycol (mw 420) | Prepolymer A | ND | 360 | ND | ND |
| 4 | Polytetramethylene glycol (mw 650) | Prepolymer A | ND | 270 | ND | ND |
| 5 | Hooker S 1023 Polyester polyol | Prepolymer A | ND | 748 hrs. | ND | ND |
| 6 | Lexorez 1100-220 Polyester polyol | Prepolymer A | ND | 250 | ND | ND |

[1] prepared by reacting 17.6%, by weight, of a mixture of mono and diricinoleate of pentaerythritol, with about 82.4%, by weight, castor oil.
[2] a TDI extended castor oil available from Conap, Inc.
ND = Not determined The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. In a separatory device capable of use in biomedical applications wherein at least one separatory membrane is secured in a housing, in a manner sufficient to perform the selected biomedical function, by means of a flexible cured polyurethane composition provided by reacting a first component comprising an NCO-terminated prepolymer with a second component comprising at least one polyol, the improvement comprising using as said polyurethane composition the reaction product of:

A. at least one of said NCO-terminated prepolymers, and

B. at least one hydroxyl-terminated lactone polyester having an average molecular weight of between about 200 and about 1000 comprising the reaction product of:

1. at least one lactone represented by the structural formula:

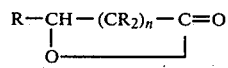

wherein n is an integer which can vary from 1 to about 10, and R is selected from the group consisting of hydrogen, alkyl, cycloalkyl, and alkoxy groups, having from about 1 to about 6 carbon atoms; and 2. at least one saturated difunctional polyol selected from the group consisting of (a) glycols represented by the structural formula:

HO—CH$_2$—(CR′$_2$)$_n$—CH$_2$—OH wherein n is an integer which can vary from about 0 to 12, and R′ is selected from the group consisting of hydrogen and an alkyl group having from about 1 to about 6 carbon atoms; and (b) cycloaliphatic polyols represented by the structural formula:

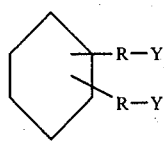

wherein R is an alkyl group having from about 1 to about 6 carbon atoms and Y is a primary hydroxyl group.

2. The separatory device of claim 1 wherein the separatory membrane comprises an assembly of a plurality of permeable continuously hollow fibers whose open terminal portions are potted in a sealing collar of said cured polyurethane composition, wherein the open terminal portions of the fibers extend through the sealing collar, the resulting potted assembly being sealed within a casing to form a separatory cell having fluid ports which allow for the passage of a first fluid through the lumen of the hollow fibers and a second fluid around and in contact with the outside of the hollow fibers, said sealing collar acting as a means for isolating the flow of said first and second fluids from one another.

3. The separatory device of claim 1 wherein (a) a plurality of separatory membrane assemblies are disposed in a spaced relationship in opposition to one another in a surface-to-surface array selected from the group consisting of parallel, pleated, concentric and spiral, to define both a first group of flow volumes and a second group of flow volumes alternating between said first group; (b) spacing means for the membrane assemblies are located in each of said flow volumes; (c) said cured polyurethane composition is employed for simultaneously defining the periphery of each of said flow volumes and for bonding together adjacent membrane assemblies and the spacing means located therebetween to form gastight peripheral walls; and (d) means are provided for separate access to, and egress from, the plurality of flow volumes in said first and second groups of flow volumes said means placing at least two adjacent flow volumes of the same group in flow communication.

4. The separatory device of any one of claims 1 to 3 wherein (1) the NCO-terminated prepolymer is the reaction product of (a) at least one polyol selected from the group consisting of polyol esters, polyether polyols, and castor oil, and (b) at least one polyfunctional isocyanate selected from the group consisting of aromatic diisocyanates, aromatic triisocyanates, and aliphatic diisocyanates; and (2) the polyol of the second component is the reaction product of caprolactone and at least one polyol selected from the group consisting of 1,6-hexane diol, 1,5-pentane diol, 1,4-butane diol, trimethylolethane, trimethylolpropane, triethanolpropane, 1,4-cyclohexane dimethanol, neopentyl glycol, and mixtures thereof; and (c) the molar ratio at which the lactone and diol is reacted is from about 1:1 to about 3:1.

5. The device of any one of claims 1 to 3 wherein the NCO-terminated prepolymer of the first component is the reaction product of a mixture of polyoxypropylene glycol and castor oil with at least one isocyanate selected from the group consisting of (1) diphenylmethane 4,4'-diisocyanate, and (2) mixtures of diphenylmethane 4,4'-diisocyanate and 3-isocyanatomethyl-3,5,5-trimethylcyclohexylisocyanate and the lactone polyester is the reaction product of caprolactone and at least one polyol selected from the group consisting of 1,6-hexane diol and trimethylol ethane.

6. The device of any one of claims 1 to 3 wherein said polyurethane composition is formed in the absence of a catalyst by the reaction of said first component and said second component.

7. In a process for preparing a separatory device capable of use in a biomedical application by securing a portion of at least one separatory membrane in a housing using a cured polyurethane composition provided by reacting a first component comprising at least one NCO-terminated prepolymer with a second component comprising at least one polyol, the improvement comprising mixing and reacting said NCO-terminated prepolymer of the first component with at least one hydroxyl-terminated lactone polyester having an average molecular weight of between about 200 and about 1000 comprising the reaction product of:

1. at least one lactone represented by the structural formula:

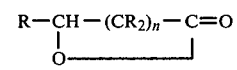

wherein n is an integer which can vary from 1 to about 10, and R is selected from the group consisting of hydrogen, alkyl, cycloalkyl, and alkoxy groups, having from about 1 to about 6 carbon atoms; and 2. at least one saturated difunctional polyol selected from the group consisting of
(a) glycols represented by the structural formula:

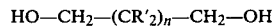

wherein n is an integer which can vary from about 0 to 12, and R' is selected from the group consisting of hydrogen and an alkyl group having from about 1 to about 6 carbon atoms; and (b) cycloaliphatic polyols represented by the structural formula:

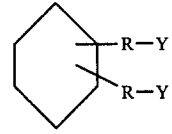

wherein R is an alkyl group having from about 1 to about 6 carbon atoms and Y is a primary hydroxyl group.

8. The process of claim 7 wherein (1) the NCO-terminated prepolymer is the reaction product of (a) at least one polyol selected from the group consisting of polyol esters, polyether polyols, and castor oil, and (b) at least one polyfunctional isocyanate selected from the group consisting of aromatic diisocyanates, aromatic triisocyanates, and aliphatic diisocyanates; and (2) the lactone polyester comprises the reaction product of caprolactone and a polyol selected from the group consisting of 1,6-hexane diol, 1,5-pentane diol, 1,4-butane diol, trimethylolpropane, triethanolpropane, trimethylolethane, 1,4-cyclohexane dimethanol, neopentyl glycol, and mixtures thereof; and (d) the molar ratio at which the lactone and diol is reacted is from about 1:1 to about 3:1.

9. The process of claim 7 wherein the NCO-terminated prepolymer of the first component is the reaction product of a mixture of polyoxypropylene glycol and castor oil with at least one isocyanate selected from the group consisting of (1) diphenylmethane 4,4'-diisocyanate, and (2) mixtures of diphenylmethane 4,4'-diisocyanate and 3-isocyanatomethyl-3,5,5-trimethylcyclohexylisocyanate; and the lactone polyolester is the reaction product of caprolactone and at least one polyol selected from the group consisting of 1,6-hexane diol and trimethylol ethane.

10. The process of claim 7, wherein the mixture of said first and second components exhibits a 2 minute mix viscosity at 25° C. of less than about 4000 cps and a gel time of not greater than about one hour at 25° C.

* * * * *